United States Patent
Fukushima et al.

(10) Patent No.: US 8,173,633 B2
(45) Date of Patent: May 8, 2012

(54) PROTEIN KINASE C ACTIVITY ENHANCER CONTAINING ALKYL ETHER DERIVATIVE OR SALT THEREOF

(75) Inventors: Tetsuo Fukushima, Toyama (JP); Akiko Takagi, Toyama (JP); Nobuo Terashima, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 147 days.

(21) Appl. No.: 12/376,296

(22) PCT Filed: Aug. 2, 2007

(86) PCT No.: PCT/JP2007/065165
§ 371 (c)(1),
(2), (4) Date: Feb. 4, 2009

(87) PCT Pub. No.: WO2008/016107
PCT Pub. Date: Feb. 7, 2008

(65) Prior Publication Data
US 2010/0184997 A1    Jul. 22, 2010

(30) Foreign Application Priority Data

Aug. 4, 2006 (JP) .................................. 2006-212722

(51) Int. Cl.
*A61K 31/4025* (2006.01)
(52) U.S. Cl. .................................................. 514/210.09
(58) Field of Classification Search .......................... None
See application file for complete search history.

(56) References Cited

U.S. PATENT DOCUMENTS

| | | |
|---|---|---|
| 6,809,092 B2 | 10/2004 | Ohmoto et al. |
| 6,825,229 B2 | 11/2004 | Etcheberrigaray et al. |
| 7,008,938 B2 | 3/2006 | Ohmoto et al. |
| 7,087,594 B2 | 8/2006 | Saitoh et al. |
| 7,468,443 B2 | 12/2008 | Saitoh et al. |
| 2003/0162964 A1 | 8/2003 | Ohmoto et al. |
| 2003/0171356 A1 | 9/2003 | Etcheberrigaray et al. |
| 2005/0009755 A1 | 1/2005 | Ohmoto et al. |
| 2005/0070521 A1 | 3/2005 | Saitoh et al. |
| 2006/0194781 A1 | 8/2006 | Saitoh et al. |
| 2006/0205709 A1* | 9/2006 | Kimura et al. ........... 514/210.19 |
| 2009/0069576 A1* | 3/2009 | Saitoh et al. .................. 548/950 |

FOREIGN PATENT DOCUMENTS

| | | | |
|---|---|---|---|
| CN | 1571786 A | | 1/2005 |
| JP | 9 507846 | | 8/1997 |
| JP | 2002 322058 | | 11/2002 |
| JP | 2005 527512 | | 9/2005 |
| JP | 2006312625 A | * | 11/2006 |
| WO | 01 55118 | | 8/2001 |
| WO | 03 035647 | | 5/2003 |
| WO | WO 03105830 A1 | * | 12/2003 |
| WO | WO 2004091605 A1 | * | 10/2004 |
| WO | WO 2006104088 A1 | * | 10/2006 |
| WO | WO 2007125913 A1 | * | 11/2007 |

OTHER PUBLICATIONS

Hirata et al., The Journal of Pharmacology and Experimental Therapeutics (2005) 314(1), pp. 252-259.*
Fukushima et al. Neurochemistry International 48 (2006) pp. 124-130.*
Harzel Ben-Shlomo, Biochemical Journal, 280(1), pp. 65-69 (1991) (abstract only).*
Takuma, Kazuhiro et al., "T-588 inhibits astrocyte apoptosis via mitogen-activated protein kinase signal pathway", European Journal of Pharmacology, vol. 399, No. 1, pp. 1-8, (2000).
Nishitani, Shinobu et al., "Branched-chain amino acids improve glucose metabolism in rats with liver cirrhosis", Am J Physiol Gastrointest Liver Physiol, vol. 288, pp. G1292-G1300, (2005).
Hofmann, Johann "Protein Kinase C Isozymes as Potential Targets for Anticancer Therapy", Current Cancer Drug Targets, vol. 4, No. 2, pp. 125-146, (2004).
Nishitani, Shinobu et al., "Leucine promotes glucose uptake in skeletal muscles of rats", Biochemical and Biophysical Research Communications, vol. 299, No. 5, pp. 693-696, (2002).
Lewin, Nancy E. et al., "Binding of [³H]Bryostatin 4 to Protein Kinase C", Biochemical Pharmacology, vol. 43, No. 9, pp. 2007-2014, (1992).
Kazanietz, Marcelo G. et al, "Binding of [26-³H]Bryostatin 1 and Analogs to Calcium-dependent and Calcium-independent Protein Kinase C Isozymes", Molecular Pharmacology, vol. 46, No. 2, pp. 374-379, (1994).
Hofmann, J. "Modulation of Protein Kinase C in Antitumor Treatment", Rev. Physiol. Biochem. Pharmacol., vol. 142, pp. 1-96, (2001).
Office Action issued Oct. 21, 2010, in Chinese Patent Application No. CN 1571786 A, filed Janaury 26, 2005 (with English-language Translation).

* cited by examiner

*Primary Examiner* — Kamal A Saeed
*Assistant Examiner* — Nyeemah A Grazier
(74) *Attorney, Agent, or Firm* — Oblon, Spivak, McClelland, Maier & Neustadt, L.L.P.

(57) ABSTRACT

Disclosed is a protein kinase C enhancer characterized by containing a benzothiophene alkyl ether derivative represented by the general formula below or a salt thereof.

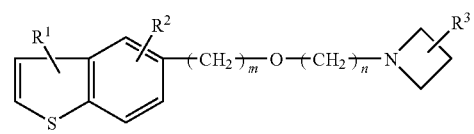

(In the formula, $R^1$ and $R^2$ may be the same or different and represent one or more groups selected from a hydrogen atom, a halogen atom, an alkyl group, an aryl group, an aralkyl group, an alkoxy group, an aryloxy group, an alkenyl group, an amino group, a heterocyclic group, an optionally protected amino group, a hydroxyl group, a carboxyl group, an oxo group and the like; $R^3$ represents an alkylamino group, an amino group, a hydroxyl group or the like; and m and n may be the same or different and represent an integer of 1-6.) This protein kinase C enhancer is useful for treatment or prevention of various diseases associated with protein kinase C.

6 Claims, 1 Drawing Sheet

CYTOSOL FRACTION 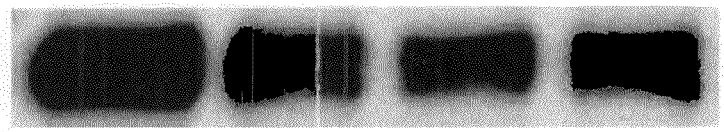
MEMBRANE FRACTION 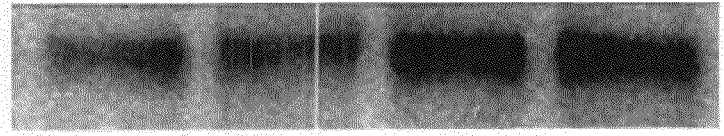
0hr　1hr　2hr　4hr
　　　T－817MA
　　　(0.1μmol/L)

PROTEIN KINASE C ACTIVITY ENHANCER CONTAINING ALKYL ETHER DERIVATIVE OR SALT THEREOF

TECHNICAL FIELD

The present invention relates to a superior protein kinase C activity enhancer containing an alkyl ether derivative or a salt thereof.

BACKGROUND ART

In mammals, protein kinase C (hereinafter referred to as "PKC") is a family consisting of 12 isoforms, and it is known to be a serine-threonine kinase that takes part in signal transduction. In addition to this, PKC is known to be involved in regulating various cell functions such as synaptic transmission, ion flux activation, secretion, cell cycle control, differentiation, multiplication, tumorigenesis, metastasis, and apoptosis. Compounds having PKC activity enhancing effect (hereinafter referred to as "PKC activity enhancers") are known to have, for example, an ameliorating effect on glucose metabolism disorder in liver cirrhosis animal models (NON-PATENT DOCUMENT 1), and an antineoplastic effect (NON-PATENT DOCUMENT 2). PKC activity enhancers are drawing much attention as therapeutic agents against various diseases, for example, glucose metabolism disorders in liver cirrhosis patients, and neoplastic diseases such as tumors.

For example, leucine is known to be PKC activity enhancer (NON-PATENT DOCUMENT 3). Branched chain amino acids (leucine and isoleucine in particular), used in branched chain amino acid replacement therapy for liver cirrhosis patients, activate PKC through PI3 kinase, promote glucose uptake by skeletal muscles, and also ameliorate glucose metabolism disorders in the liver cirrhosis rat model (NON-PATENT DOCUMENT 1).

For example, bryostatin and gnidimacrin are also known as PKC activity enhancers. Bryostatin binds to PKC (NON-PATENT DOCUMENT 4), activates PKC isozymes in vitro (NON-PATENT DOCUMENT 5), and shows antineoplastic effect (NON-PATENT DOCUMENT 6).

The alkyl ether derivatives described in the present application have been reported to have nerve protective activity, nerve regenerative activity, and neurite outgrowth promoting activity (Patent document 1). However, it is not known so far that they enhance PKC activity.

PATENT DOCUMENT 1: WO 03/035647
NON-PATENT DOCUMENT 1: Am. J. Physiol. Gastrointest. Liver. Physiol., 2005, Vol. 288, p. G1292-1300
NON-PATENT DOCUMENT 2: Curr. Cancer Drug Targets, 2004, Vol. 4, p. 125-146
NON-PATENT DOCUMENT 3: Biochem. Biophys. Res. Commun., 2002, Vol. 299, No. 5, p. 693-696
NON-PATENT DOCUMENT 4: Biochem. Pharmacol., 1992, Vol. 43, No. 9, p. 2007-2014
NON-PATENT DOCUMENT 5: Mol. Pharmacol., 1994, Vol. 46, No. 2, p. 374-379
NON-PATENT DOCUMENT 6: Rev. Physiol. Biochem. Pharmacol., 2001, Vol. 142, p. 1-96

DISCLOSURE OF THE INVENTION

Problems to be Solved by the Invention

There is a demand for a superior PKC activity enhancer with fewer side effects.

Means for Solving the Problems

Against the above background, the present inventors found that benzothiophene alkyl ether derivatives represented by general formula [1] and salts thereof show PKC activity enhancing effect and are therefore useful as PKC activity enhancers, and achieved the present invention.

[Formula 1]

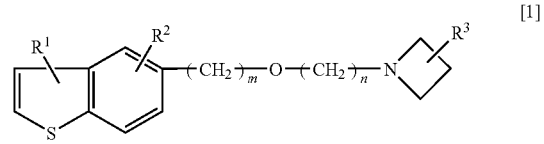

In the formula, $R^1$ and $R^2$ may be the same or different and each represents one or more groups selected from a hydrogen atom, a halogen atom, an optionally substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an optionally protected amino, hydroxyl or carboxyl group, a nitro group, and an oxo group; $R^3$ represents an optionally substituted alkylamino group or an optionally protected amino or hydroxyl group; and m and n may be the same or different and each represents an integer of 1 to 6.

Advantages of the Invention

The alkyl ether derivative represented by general formula [1] or a salt thereof, of the present invention shows PKC activity enhancing effect and is useful in treatment or prevention of various diseases where PKC is involved, for example, glucose metabolism disorder in liver cirrhosis patients, and neoplastic diseases such as tumors.

BEST MODE FOR CARRYING OUT THE INVENTION

The present invention is disclosed in more detail below.
The terms used in the present description have the meanings given below, unless specified otherwise.

"A halogen atom" means a fluorine atom, a chlorine atom, a bromine atom or an iodine atom; "an alkyl group" means a straight chain or branched chain $C_{1-12}$alkyl group such as methyl, ethyl, propyl, isopropyl, butyl, isobutyl, tert-butyl, pentyl, hexyl, heptyl and octyl; "a lower alkyl group" means a straight chain or branched chain $C_{1-6}$alkyl group such as methyl, ethyl, propyl, isopropyl, butyl, isobutyl, tert-butyl, pentyl and hexyl; "an alkenyl group" means a $C_{2-12}$alkenyl group such as vinyl, propenyl, butenyl, pentenyl, hexenyl, heptenyl and octenyl; "a lower alkenyl group" means a $C_{2-6}$alkenyl group such as vinyl, propenyl, butenyl, pentenyl and hexenyl; "an acylalkyl group" means an acyl$C_{1-6}$alkyl group such as acetylmethyl, benzoylmethyl, p-nitrobenzoylmethyl, p-bromobenzoylmethyl, p-methoxybenzoylmethyl and 1-benzoylethyl; "an acyloxyalkyl group" means an acyloxy$C_{1-6}$alkyl group such as acetoxymethyl, propionyloxymethyl and pivaloyloxymethyl; "an arylthioalkyl group" means an arylthio$C_{1-6}$alkyl group such as phenylsulfenylmethyl and 2-(p-nitrophenylsulfenyl)ethyl; "an arylsulfonylalkyl group" means an arylsulfonyl$C_{1-6}$alkyl group such as p-toluenesulfonylethyl; "a nitrogen-containing heterocyclic alkyl group" means a nitrogen-containing heterocyclic $C_{1-6}$alkyl group such as phthalimidomethyl and succinimidomethyl; "a cycloalkyl group" means a $C_{3-8}$cycloalkyl group such as cyclopropyl, cyclobutyl, cyclopentyl and cyclohexyl; "an alkylthioalkyl group" means a $C_{1-6}$alkylthio$C_{1-6}$alkyl group such as methylthiomethyl, ethylthiomethyl and propylthiomethyl; "an alkoxyalkyl group" means a $C_{1-6}$alkyloxyalkyl group such as methoxymethyl and 1-ethoxyethyl; and "an aralkyloxyalkyl group" means an ar$C_{1-6}$alkyloxy$C_{1-6}$alkyl group such as benzyloxymethyl and phenethyloxymethyl;

"an alkoxy group" means a straight chain or branched chain $C_{1-12}$alkyloxy group such as methoxy, ethoxy, propoxy, isopropoxy, butoxy, isobutoxy, tert-butoxy, pentyloxy, hexyloxy, heptyloxy and octyloxy; "a lower alkoxy group" means a straight chain or branched chain $C_{1-6}$alkyloxy group such as methoxy, ethoxy, propoxy, isopropoxy, butoxy, isobutoxy, tert-butoxy, pentyloxy and hexyloxy; "an alkenyloxy group" means a $C_{2-12}$alkenyloxy group such as vinyloxy, propenyloxy, butenyloxy, pentenyloxy, hexenyloxy, heptenyloxy and octenyloxy;

"an alkylthio group" means a $C_{1-12}$alkylthio group such as methylthio, ethylthio, propylthio, isopropylthio, butylthio, isobutylthio, tert-butylthio, pentylthio, hexylthio, heptylthio and octylthio; and "a lower alkylthio group" means a $C_{1-6}$alkylthio group such as methylthio, ethylthio, propylthio, isopropylthio, butylthio, isobutylthio, tert-butylthio, pentylthio and hexylthio;

"an aryl group" means a phenyl, naphthyl, indanyl or indenyl group; "an aryloxy group" means a phenyloxy, naphthyloxy, indanyloxy or indenyloxy group; "an aralkyl group" means an ar$C_{1-6}$alkyl group such as benzyl, diphenylmethyl, trityl and phenethyl; "an arylthio group" means a phenylthio, naphthylthio, indanylthio or indenylthio group;

"an acyl group" means a formyl group, a $C_{2-12}$alkanoyl group such as acetyl, isovaleryl, propionyl and pivaloyl, an ar$C_{1-6}$alkylcarbonyl group such as benzylcarbonyl, and an aroyl group such as benzoyl and naphthoyl; "an alkyloxycarbonyl group" means a straight-chain or branched-chain $C_{1-12}$alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; "an aralkyloxycarbonyl group" means an ar$C_{1-6}$alkyloxycarbonyl group such as benzyloxy carbonyl and phenethyloxycarbonyl; "an aryloxycarbonyl group" means a group such as phenyloxycarbonyl; "a heterocyclic oxycarbonyl group" means a group such as 2-furfuryloxycarbonyl and 8-quinolyloxycarbonyl;

"an alkylsulfonyl group" means a $C_{1-12}$alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, heptylsulfonyl and octylsulfonyl; "a lower alkylsulfonyl group" means a $C_{1-6}$alkylsulfonyl group such as methylsulfonyl, ethylsulfonyl and propylsulfonyl; "an arylsulfonyl group" means a group such as phenylsulfonyl, p-toluenesulfonyl and naphthylsulfonyl;

"an alkylamino group" means a mono- or di-$C_{1-6}$alkylamino group such as methylamino, ethylamino, propylamino, isopropylamino, butylamino, dimethylamino, diethylamino, diisopropylamino and dibutylamino;

"a heterocyclic group" means a 5-member or 6-member, fused ring or bridged ring heterocyclic group having at least one heteroatom selected from a nitrogen atom, an oxygen atom and a sulfur atom, for example, pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl and 1,4-benzodioxanyl;

"an oxygen-containing heterocyclic group" means a group such as 2-tetrahydropyranyl and 2-tetrahydrofuranyl; "a sulfur-containing heterocyclic group" means a group such as tetrahydrothiopyranyl; "a substituted silyl group" means a group such as trimethylsilyl, triethylsilyl and tributylsilyl; "an alkylsilylalkyl group" means a $C_{1-6}$alkylsilyl$C_{1-6}$alkyl group such as 2-(trimethylsilyl)ethyl.

Amino-protecting groups include all groups that may be used as protecting groups for amino groups, for example, the groups described by W. Greene et al. in Protective Groups in Organic Synthesis, $3^{rd}$ edition, page 494-615, 1999, John Wiley & Sons, Inc. Specific examples include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkylsulfonyl group, an arylsulfonyl group and a substituted silyl group.

The hydroxyl protecting group includes all groups that may be used as protecting groups for hydroxyl groups, for example, the groups described by W. Greene et al. in Protective Groups in Organic Synthesis, $3^{rd}$ edition, page 17-245, 1999, John Wiley & Sons, Inc. Specific examples include an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkylsulfonyl group, an arylsulfonyl group and a substituted silyl group.

The carboxyl protecting group includes all groups that may be used as protecting groups for carboxyl groups, for example, the groups described by W. Greene et al. in Protective Groups in Organic Synthesis, $3^{rd}$ edition, page 369-453, 1999, John Wiley & Sons, Inc. Specific examples include an alkyl group, an alkenyl group, an aryl group, an aralkyl group, an acylalkyl group, an arylthioalkyl group, an arylsulfonylalkyl group, an oxygen-containing heterocyclic group, an alkylsilylalkyl group, an acyloxyalkyl group, a nitrogen-containing heterocyclic alkyl group, a cycloalkyl group, an alkoxyalkyl group, an aralkyloxyalkyl group, an alkylthioalkyl group and a substituted silyl group.

Examples of substituents for the alkyl group, the aryl group, the aralkyl group, the alkoxy group, the aryloxy group, the alkylthio group, the arylthio group, the alkenyl group, the alkenyloxy group, the amino group, the alkylsulfonyl group, the arylsulfonyl group, the carbamoyl group and the heterocyclic group at $R^1$ and $R^2$, and for the alkylamino group at $R^3$, are groups selected from a halogen atom, lower alkyl group, a cycloalkyl group, an aryl group, a lower alkoxy group, an aryloxy group, a lower alkylthio group, an arylthio group, a lower alkenyl group, a lower alkylsulfonyl group, an arylsulfonyl group, an alkylamino group, an optionally protected amino group, an optionally protected hydroxyl group, an optionally protected carboxyl group, an acyl group, a heterocyclic group, and the like.

The salt of the compound of general formula [1] may be a commonly known salt at a basic group such as an amino group, or salt at an acidic group such as a hydroxyl or carboxyl group.

Examples of salts at basic groups include salts of mineral acids such as hydrochloric acid, hydrobromic acid, nitric acid and sulfuric acid; salts of organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts of sulfonic acids such as methane sulfonic acid, benzene sulfonic acid, p-toluene sulfonic acid, mesitylene sulfonic acid and naphthalene sulfonic acid.

Examples of salts at acidic groups include salts of alkali metals such as sodium and potassium; salts of alkali earth metals such as calcium and magnesium; ammonium salts; salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the salts described above, pharmacologically acceptable salts are preferable.

When the alkyl ether derivatives of general formula [1] and salts thereof have isomers such as optical isomers, geometric isomers and tautomers, the present invention covers all such isomers. The invention also covers hydrates, solvates, and all possible crystalline forms.

The compounds listed below are preferable as the alkyl ether derivatives of general formula [1], and salts thereof, of the present invention.

The compound wherein $R^1$ is a hydrogen atom is preferable.

The compound wherein $R^2$ is a hydrogen atom, a halogen atom or an alkoxy group is preferable, and the compound wherein $R^2$ is a hydrogen atom is more preferable.

The compound wherein $R^3$ is a hydroxyl group is preferable.

The compound wherein m is 2 is preferable.

The compound wherein n is 2 or 3 is preferable, and the compound where n is 3 is more preferable.

The compound wherein $R^1$ and $R^2$ are a hydrogen atom, $R^3$ is a hydroxyl group, m is 2, and n is 3 is even more preferable.

The compound wherein the alkyl ether derivative of general formula [1] or a salt thereof is 1-(3-(2-(1-benzothiophen-5-yl)ethoxy)propyl)azetidin-3-ol (hereinafter referred to as "T-817") or a salt thereof is even more preferable, and the maleic acid salt of T-817 (hereinafter referred to as "T-817MA") is the most preferable.

The alkyl ether derivative of general formula [1], or a salt thereof, of the present invention, has PKC activity enhancing effect, and drugs containing the alkyl ether derivative of general formula [1], or a salt thereof, are useful in treatment or prevention of diseases where the PKC activity enhancement is effective.

The alkyl ether derivative of general formula [1] or a salt thereof used in the present invention may be prepared by a publicly known method, a suitable combination of the known methods, or by the method described in PATENT DOCUMENT 1.

The alkyl ether derivative of general formula [1] or a salt thereof used in the present invention may be made into a drug product, such as an oral drug (tablet, capsule, powder, granule, fine granule, pill, suspension, emulsion, solution, syrup, etc.), injections, eye drops and the like, by compounding various drug additives such as excipients, binders, disintegrators, disintegration inhibitors, anti-caking and anti-sticking agents, lubricants, absorbing/adsorbing carriers, solvents, bulking agents, isotonic agents, solubilizers, emulsifiers, suspending agents, thickeners, coating agents, absorption enhancers, gelation/coagulation promoters, light stabilizers, preservatives, desiccants, emulsion/suspension/dispersion stabilizers, coloration preventing agents, deoxidizers/antioxidants, flavoring agents, coloring agents, whipping agents, antifoaming agents, soothing agents, antistatic agents and buffering/pH regulating agents.

The above-mentioned drug products are prepared by ordinary methods.

The solid oral drug products such as tablets, powders and granules, may be prepared by conventional methods, by adding drug additives for solid drug products, for example, excipients such as lactose, sucrose, sodium chloride, glucose, starch, calcium carbonate, kaolin, crystalline cellulose, anhydrous dibasic calcium phosphate, partially alpha starch, corn starch and alginic acid; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, sodium alginate, gum arabic, hydroxypropylmethylcellulose, hydroxypropylcellulose, water and ethanol; disintegrators such as dry starch, alginic acid, agar powder, starch, cross-linked polyvinylpyrrolidone, cross-linked carboxymethylcellulose sodium, carboxymethylcellulose calcium and sodium starch glycolate; disintegration inhibitors such as stearyl alcohol, stearic acid, cocoa butter and hydrogenated oil; anti-caking/anti-sticking agents such as aluminum silicate, calcium hydrogen phosphate, magnesium oxide, talc and anhydrous silicic acid; lubricants such as carnauba wax, light anhydrous silicic acid, aluminum silicate, magnesium silicate, hardened oil, hardened vegetable oil derivative, sesame oil, bleached beeswax, titanium oxide, dry aluminum hydroxide gel, stearic acid, calcium stearate, magnesium stearate, talc, calcium hydrogen phosphate, sodium lauryl sulfate and polyethylene glycol; absorption enhancers such as quaternary ammonium salts, sodium lauryl sulfate, urea and enzymes; absorption/adsorption carriers such as starch, lactose, kaolin, bentonite, anhydrous silicic acid, hydrated silicon dioxide, magnesium aluminometasilicate and colloidal silicic acid.

In the case of tablets, if needed, they may be made into ordinary coated tablets, such as sugarcoated tablets, gelatincoated tablets, gastric-coated tablets, enteric-coated tablets, and water-soluble film-coated tablets.

Capsules are prepared by first mixing with the various above-listed drug products, and packing into hard gelatin capsules, soft capsules, and the like.

Aqueous or oil-based suspensions, solutions, syrups and elixirs may be also prepared, using various aforementioned additives for liquid drug products, for example, solvents, bulking agents, isotonic agents, solubilizers, emulsifiers, suspending agents and thickeners.

Injections may be prepared by a conventional method, using drug additives for liquid drug products, for example, diluents such as water, ethyl alcohol, Macrogol, propylene glycol, citric acid, acetic acid, phosphoric acid, lactic acid, sodium lactate, sulfuric acid and sodium hydroxide; pH regulators and buffering agents such as sodium citrate, sodium acetate and sodium phosphate; stabilizers such as sodium pyrosulfite, ethylenediamine tetraacetic acid, thioglycolic acid and thiolactic acid; isotonic agents such as common salt, glucose, mannitol and glycerol; solubilizers such as carboxymethylcellulose sodium, propylene glycol, sodium benzoate, benzyl benzoate, urethane, ethanolamine and glycerol;

soothing agents such as calcium gluconate, chlorobutanol, glucose and benzyl alcohol; and local anesthetics.

Eye drops may be prepared by a conventional method, by suitably compounding with, for example, preservatives such as chlorobutanol, sodium dehydroacetate, benzalkonium chloride, cetylpyridinium chloride, phenethyl alcohol, methyl parahydroxybenzoate and benzethonium chloride; buffering agents such as borax, boric acid and potassium dihydrogen phosphate; thickeners such as methylcellulose, hydroxyethylcellulose, carboxymethylcellulose, hydroxypropylmethylcellulose, polyvinyl alcohol, carboxymethylcellulose sodium and chondroitin sulfate; solubilizers such as polysorbate 80 and polyoxyethylene hardened castor oil 60; stabilizers such as sodium edetate and sodium hydrogen sulfite; and isotonic agents such as sodium chloride, potassium chloride and glycerol.

There is no particular restriction on the method of administering the above-mentioned drug products; it has to be decided, taking into consideration the dosage form, the age, sex and other conditions of the patient, and the severity of the symptoms.

The dose of the active ingredient of the drug product of the present invention is decided suitably, according to the dose regimen, age and sex of the patient, pattern of the disease, and other conditions. However, usually, 0.1 to 500 mg/day may be given to an adult, at once or in a few administrations.

EXAMPLES

The present invention is described below, with the help of some experimental examples and formulation examples. However, these examples do not in any way limit the scope of the invention.

In these experiments, T-817MA was used as the test substance.

Experimental Example 1

PKC Activity Enhancing Effect in Cultured Cells

The PKC activity was determined, according to the method of Etcheberrigaray et al. (Proceedings of the National Academy of Sciences of the United States of America, 2004, Vol. 101, No. 30, p. 11141-11146), as applicable. At the time of activation, PKC migrates from the cytoplasm to membranes. The PKC level in the membrane fraction over that in the cytosol fraction was taken as the index of PKC activation. In this experiment, the activity of PKC$\epsilon$, a known isoform of PKC, was measured.

Cultured cells were prepared following the method of Hirata et al. (J. Pharmacol. Exp. Ther., 2005, Vol. 314, No. 1, p. 252-259).

The cerebral cortex was removed from 18-day fetuses of Wistar/ST rats, and incubated in phosphate-buffered physiological saline (hereinafter referred to as "PBS") containing 0.25% trypsin and 40 Kunitz units/mL DNase I, for 20 minutes at 37° C. After that, an equal mixture of fetal bovine serum (manufactured by JRH Co.) and Dulbecco's Modified Eagle Medium (hereinafter referred to as "DMEM") was added, and cells in the suspension were dispersed by pipetting. This suspension was filtered through a lens paper, centrifuged for 5 minutes at 1000 rpm, and the cells dispersed again by pipetting in DMEM containing 10% fetal bovine serum. The cells were then inoculated at a density of $4\times10^5$ cells/mL in 5 mL of medium in a 60 mm tissue culture dish that had been coated with poly-L lysine, and cultured. On Day 2 from the start of the culturing, 50 µL of 1 mmol/L AraC solution was added to each dish. 24 hours later, the medium was changed to 5 mL of DMEM containing 10% fetal bovine serum.

On Day 8 from the start of the culturing, T-817MA was added to the cells to a final concentration of 0.1 µmol/L, in terms of T-817, After this addition, the cells were washed with PBS at 0 (untreated), 1, 2 and 4 hours. Then, using a cell scraper, the cells were gathered into an extraction buffer (20 mmol/L Tris-HCl, pH 7.5, 2 mmol/L EDTA, 2 mmol/L EGTA, 5 mmol/L DTT, 0.32 mol/L sucrose, and 1/100 volume of protease inhibitor cocktail (manufactured by SIGMA)). The cell extract was ultrasonicated and the supernatant obtained after centrifuging for 20 minutes at 12000×g was designated as the cytosol fraction. The extraction buffer containing 1% Triton X-100 was added to the pellet. After ultrasonication, it was left standing on ice for 45 minutes. It was again centrifuged for 20 minutes at 12000×g, and the supernatant obtained was designated as the membrane fraction. The protein concentration in the cytosol fraction and the membrane fraction was measured, and the protein content in each sample was adjusted to a certain constant level with the extraction buffer or the extraction buffer containing Triton X-100, These samples were then diluted with electrophoresis buffer containing mercaptoethanol (manufactured by Wako Pure Chemical Industries Ltd.) and SDS-PAGE (40 mA, 30 minutes) was carried on 10% polyacrylamide gel. After completing the SDS-PAGE, the protein on the gel was transferred to a PVDF membrane (150 mA, 90 minutes). The membrane was shaken for 60 minutes in PBST (PBS containing 0.1% Tween 20) containing 5% skim milk. After that, the membrane was immersed in PBS containing anti-mouse PKC$\epsilon$ antibody (manufactured by BD Transduction Laboratories, diluted 500 times) and left standing for 90 minutes. Then, after washing the membrane with PBST, it was shaken for 90 minutes in PBST containing HRP-labeled anti-mouse IgG antibody (manufactured by GE Healthcare Bio-Sciences, diluted 2500 times). Then, after washing with PBST, the membrane was treated with ECL plus reagent (manufactured by GE Healthcare Bio-Sciences) and the luminescence was detected by a Lumino Image Analyzer. The PKC$\epsilon$ bands of the samples were compared. The results are shown in FIG. 1.

The PKC$\epsilon$ was seen to have migrated from the cytoplasm to membranes in 2 hours and 4 hours after the cells were treated with T-817MA. The migration of the PKC from the cytoplasm to the membrane may be taken as an index of activation. Therefore, it was demonstrated that T-817MA had PKC$\epsilon$ activity enhancing effect.

Formulation Example 1

A mixture of 50 mg T-817MA, 20 mg lactose, 25 mg corn starch, and 40 mg Avicel PH101 (manufactured by Asahi Kasei Corporation) was blended using a 5% aqueous solution of polyvinylpyrrolidone K30, After drying the mixture at 60° C., a mixture of 10 mg of Kollidon CL (manufactured by BASF Co., Ltd.), 10 mg Avicel PH302 (manufactured by Asahi Kasei Corporation), 18 mg light anhydrous silicic acid, and 2 mg magnesium stearate was mixed with it, and tabled into circular tablets of diameter 7 mm, each weighing 175 mg and containing 50 mg of T-817MA.

Formulation Example 2

A mixture of 50 mg T-817MA, 20 mg lactose and 53 mg corn starch was blended using a 5% aqueous solution of polyvinylpyrrolidone K30 and dried at 60° C. After that a mixture of 7 mg Kollidon CL (manufactured by BASF Co., Ltd.), 18 mg Avicel PH302 (manufactured by Asahi Kasei Corporation), and 2 mg of magnesium stearate was mixed with it. 150 mg of this mixture was filled per capsule in No. 4 gelatin capsules to prepare drug capsules.

BRIEF DESCRIPTION OF THE DRAWING

FIG. 1 is the result of western blotting in the experiment where PKC activity in cultured cells was measured.

Industrial Applicability

The alkyl ether derivative, or salt thereof, of the present invention shows PKC activity enhancing effect and is useful in treatment or prevention of various diseases where PKC is involved, for example, glucose metabolism disorder in liver cirrhosis patients, and neoplastic diseases such as tumors.

The invention claimed is:

1. A method for treatment of glucose metabolism disorder in a subject having liver cirrhosis or treatment of a neoplastic disease, comprising:
    administering to a subject in need thereof a benzothiophene alkyl ether compound represented by general formula (I):

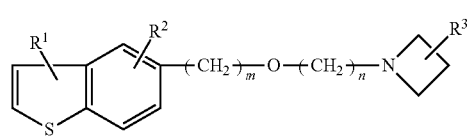

(I)

wherein,
    $R^1$ and $R^2$ may be the same or different and each represents one or more groups selected from the group consisting of a hydrogen atom, a halogen atom, an optionally substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an optionally protected amino, hydroxyl or carboxyl group, a nitro group, and an oxo group;
    $R^3$ represents an optionally substituted alkylamino group, or an optionally protected amino or hydroxyl group; and
    m and n may be the same or different and each represents an integer of 1 to 6, or
a pharmaceutically acceptable salt thereof.

2. The method according to claim 1 comprising administering a benzothiophene alkyl ether compound wherein $R^1$ is a hydrogen atom, and $R^2$ is a hydrogen atom, a halogen atom, or an alkoxy group, or a pharmaceutically acceptable salt thereof.

3. The method according to claim 1 comprising administering a benzothiophene alkyl ether compound wherein m is 2, and n is 2 or 3, or a pharmaceutically acceptable salt thereof.

4. The method according to claim 1 comprising administering a benzothiophene alkyl ether compound wherein $R^2$ is a hydrogen atom, $R^3$ is a hydroxyl group, and n is 3, or a pharmaceutically acceptable salt thereof.

5. The method according to claim 1, comprising administering a benzothiophene alkyl ether compound wherein the benzothiophene alkyl ether compound is 1-(3-(2-(1-benzothiophen-5-yl)ethoxy)propyl)azetidin-3-ol or a pharmaceutically acceptable salt thereof.

6. The method according to claim 1, wherein the neoplastic disease is a tumor.

* * * * *